(12) United States Patent
Beker et al.

(10) Patent No.: US 7,151,957 B2
(45) Date of Patent: Dec. 19, 2006

(54) METHOD AND DEVICE FOR ANALYZING A PERIODIC OR SEMI-PERIODIC SIGNAL

(75) Inventors: Amir Beker, Rosh Ha'ayin (IL); Assaf Hasson, Tel Aviv (IL); Tamir Ben David, Tel Aviv (IL)

(73) Assignee: BSP Biological Signal Processing Ltd., Tel-Aviv (IL)

( * ) Notice: Subject to any disclaimer, the term of this patent is extended or adjusted under 35 U.S.C. 154(b) by 727 days.

(21) Appl. No.: 10/168,673

(22) PCT Filed: Dec. 28, 2000

(86) PCT No.: PCT/IL00/00871

§ 371 (c)(1),
(2), (4) Date: Jun. 25, 2002

(87) PCT Pub. No.: WO01/49160

PCT Pub. Date: Jul. 12, 2001

(65) Prior Publication Data
US 2003/0208129 A1    Nov. 6, 2003

(30) Foreign Application Priority Data
Dec. 29, 1999    (IL) .................................... 133780

(51) Int. Cl.
*A61B 5/04*    (2006.01)
(52) U.S. Cl. .................................... 600/509
(58) Field of Classification Search ............... 600/509, 600/517; 702/189–190, 199
See application file for complete search history.

(56) References Cited
U.S. PATENT DOCUMENTS
4,732,158 A    3/1988    Sadeh
4,954,732 A    9/1990    Surauer et al.
5,609,158 A *  3/1997    Chan .......................... 600/518
5,966,684 A    10/1999   Richardson et al.

OTHER PUBLICATIONS

Beker et al, "Analysis of High Frequency QRS Potentials During Exercise Testing", Proc. On Computers in Cardiology, *IEEE Computer Soc.*, 1992, pp. 33-35.
Becker et al., "Analysis of High Frequency QRS Potential During Exercise Testing in Patients with Coronary Artery Disease and in Healthy Subjects", *PACE*, 12:2040-2050, 1996.
Abboud, Shimon, "High-Frequency Electrocardiogram Analysis of the Entire QRS in the Diagnosis and Assessment of Coronary Artery Disease", *Progress in Cardiovascular Diseases*, vol. XXXV, No. 5., Mar./Apr. 1993.
Becker et al, "Spectral Analysis of the High Resolution QRS Complex During Excersize-Induced Ischemia", *A.N.E.*, 1(4):386-392, 1996.

* cited by examiner

*Primary Examiner*—Mark Bockelman

(57) ABSTRACT

A device for reducing noise in signals having successive substantially repetitive portions, comprising: an iterative averager operative to superimpose and average said substantially repetitive portions to produce a running average thereof, and an iteration ender comprising a noise analyzer for determining a noise level in said running average and ending operation of said iterative averager when said noise level reaches a predetermined level. Also, a method of obtaining an indication of ischemia in a patient using an ECG signal therefrom, the method comprising: extracting an ECG signal over a duration, extracting from said ECG signal a series of QRS complexes over said duration, extracting high frequency components of said QRS complexes, analyzing said high frequency components over said duration for at least one of a predetermined quality, and inferring from said predetermined quality an indication of ischemia.

19 Claims, 7 Drawing Sheets

METHOD AND DEVICE FOR ANALYZING A PERIODIC OR SEMI-PERIODIC SIGNAL

FIELD OF THE INVENTION

The present invention relates to a method and device for analyzing a periodic or semiperiodic signal and more particularly but not exclusively to analyzing a signal having the form of a typical electrocardiograph signal, again more particularly but not exclusively to obtaining an improved signal to noise ratio from such a signal.

BACKGROUND OF THE INVENTION

The electrocardiograph (ECG) signal describes the electrical activity of the cardiac muscle as it generates the various stages of the heart wave. Each cycle in the ECG signal may be subdivided into segments corresponding to stages of the heart wave, such as the P wave, the QRS complex, the T wave, the ST segment etc. Thus, the P wave of the ECG signal is due to depolarization of the atria, the QRS complex to depolarization of the ventricles, and the T wave to repolarization of the ventricles. Detection of an altered ECG signal is an important non-invasive tool in the diagnosis of cardiac abnormalities. Analysis of the ECG signal usually focuses on the ST segment due to its low-noise and its well-known correlation with cardiac abnormalities such as coronary artery disease (CAD). As physical stress is known to introduce features into the ECG signal indicative of CAD not present in signals obtained at rest it is common to obtain an ECG signal from a subject during a stress test comprising phases of rest, exercise and recovery from exercise.

In order to obtain sufficient information to provide usefull diagnostic information from ECG measurements it is thus current practice to obtain data A high level of alignment is a prerequisite for any effective averaging process. Thus, filtering the signal, before performing the alignment, as suggested in the above method, makes it practically inapplicable to signals, such as the HF component of ECG, where the signal to noise ratio in the frequencies of interest is very high.

Thus the methods known in the art are not effective in the analysis of signals with a varying level of relatively high noise, especially when transient changes in the signals are of importance. A typical example of such a signal is the HF ECG component obtained during the above-mentioned exercise test, which has been shown to be of importance in early detection of ischemia—it has been shown by Beker et al. (Proceedings on computers in Cardiology, IEEE Computer Society, 33–35,1992) and Beker et al. (Pacing and Clinical electrophysiology 12:2040, 1996) that decrease in the energy level of the HF component of the QRS interval during the course of the exercise test may be indicative of ischemia.

There is therefore a need for a method to enhance the signal-to-noise ratio in periodic or semi-periodic signals, such as ECG signals—a method that will eliminate or substantially reduce the disadvantages of the prior art methods.

SUMMARY OF THE INVENTION

Embodiments of the present invention provide a process, referred to herein as "adaptive averaging", for effecting an improvement in the signal-to-noise ratio of periodic or semi-periodic signals. Preferred embodiments comprise the following features:

1. Effective noise reduction, without any a-priori limit on the improvement of the signal to noise ratio.
2. Reduced attenuation of transient changes in the signal, and
3. Dynamic response to changes in the noise level of the signal.

According to a first aspect of the present invention there is thus provided a device for reducing noise in signals having successive substantially repetitive portions, comprising:

an iterative averager operative to superimpose and average said substantially repetitive portions to produce a running average thereof, and an iteration ender comprising a noise analyzer for determining a noise level in said running average and ending operation of said iterative averager when said noise level reaches a predetermined level.

Preferably, said iterative averager is operative to take said successive portions in successive iterative steps.

Preferably, the device further comprises an aligner for aligning at least some of said substantially repetitive portions one with another, wherein said signal comprises first frequency and second frequency components and said aligner comprises a first frequency correlated band pass filter and a second frequency correlated band pass filter to extract respective first and second frequency components, thereby to use said first frequency components to locate an alignment point in successive portions and to use said alignment point to align said second frequency components.

Preferably, said iteration ender is further operative to end said operation of said iterative averager when said repetitive portions are exhausted.

Preferably, said iteration ender is further operative to end said operation of said iterative averager when said running average reaches a preset maximum of included repetitive portions.

Preferably, the device further comprises a repetitive portion selector for selecting repetitive portions for passing to said iterative averager, the repetitive portion selector comprising a reference portion store for storing a reference portion, a cross correlator for computing a cross correlation between a current repetitive portion and said reference portion, and a comparator for comparing a result of said cross-correlation with a predetermined threshold to produce a comparison output, and wherein said selector is operable to pass said current repetitive portion to said iterative averager in accordance with said comparison output.

Preferably, the device further comprises a reference portion determination unit associated with said repetitive portion selector, operable to determine as a reference portion any one of a group comprising a first repetitive portion of a current length of said signal, a final result of a running average of a previous set of iterations and a prior determined typical wave.

Preferably, said reference portion determination unit is operable to dynamically change between members of said group over the course of a set of iterations.

Preferably, said reference portion determination unit further comprises a reference portion updater for dynamically updating said reference portion during the course of a set of iterations.

Preferably, the device further comprises a reference portion determiner, said reference portion determiner comprising, a first store for storing a first set of repetitive portions from said signal, a second store for storing a second set of repetitive portions from said signal, a cross correlator for cross-correlating repetitive portions from said second set in turn with repetitive portions from said first set to produce a plurality of cross-correlation results for respective repetitive portions in said second set, and a reference selector for selecting one of said repetitive portions in said second set as a reference portion in accordance with its respective cross-correlation results.

Preferably, said reference selector comprises a threshold level comparator for comparing each cross-correlation result with a threshold and which is operable to select as said reference portion a repetitive portion having a highest number of respective cross-correlation results exceeding said threshold.

Preferably, the device further comprises a summation unit for summing cross-correlation results of respective repetitive portions and which reference selector is operable to select as a reference portion a repetitive portion having the highest sum of respective cross-correlation results.

Preferably, said reference selector comprises:

a threshold level comparator for comparing each cross-correlation result with a threshold, and a summation unit for summing cross-correlation results of respective repetitive portions exceeding said threshold, and which reference selector is operable to select as a reference portion a repetitive portion having a highest sum of respective cross-correlation results.

Preferably, the device further comprises a signal extractor for extracting said repetitive portion.

Preferably, the device further comprises an RMS computation unit for calculation of the energy level of segments of wave obtained by averaging a series of said repetitive portions.

Preferably, the device further comprises an RMS value analysis unit for detecting a falloff in said RMS energy value over succeeding averages.

Preferably, the device further comprises a cross-correlation unit for computing the cross correlation coefficient of an average of a series of said repetitive portions and a reference wave.

Preferably, the device further comprises a cross-correlation value analysis unit for detecting a falloff in said cross-correlation value over succeeding averages.

Preferably, said aligner further comprises a cross-correlator for cross-correlating a current input with said running average at a plurality of successive alignments and for aligning said signal on the basis of an alignment giving a maximum cross-correlation.

Preferably, said aligner further comprises:

an interpolator for interpolating between said cross-correlations at said successive alignments to determine a higher accuracy sub-sample alignment, and a wave shifter for shifting said current input in accordance with said determined sub-sample alignment.

According to a second aspect of the present invention, there is provided a device for reducing noise in signals having successive substantially repetitive portions, comprising:

an aligner for aligning at least some of said substantially repetitive portions one with another, a repetitive portion selector for selecting repetitive portions for passing to said iterative averager on the basis of a comparison with a reference portion, and an iterative averager operative to superimpose and average said aligned, selected portions to produce a running average thereof.

Preferably, the device further comprises a repetitive portion selector for selecting repetitive portions for passing to said iterative averager, the repetitive portion selector comprising a reference portion store for storing a reference portion, a cross correlator for computing the cross correlation between a current repetitive portion and said reference portion, and a comparator for comparing a result of said cross-correlation with a predetermined threshold to produce a comparison output, and wherein said selector is operable to pass said current repetitive portion to said iterative averager in accordance with said comparison output.

Preferably, the device further comprises a reference portion determination unit associated with said repetitive portion selector, operable to determine as a reference portion any one of a group comprising a first repetitive portion of a current length of said signal, a final result of a running average of a previous set of iterations and a prior determined typical wave.

Preferably, said reference portion determination unit is operable to dynamically change between members of said group over a course of a set of iterations.

Preferably, said reference portion determination unit further comprises a reference portion updater for dynamically updating said reference portion during a course of a set of iterations.

Preferably, the device further comprises a reference portion determiner, said reference portion determiner comprising, a first store for storing a first set of repetitive portions from said signal, a second store for storing a second set of repetitive portions from said signal, a cross-correlator for cross-correlating repetitive portions from said second set in turn with repetitive portions from said first set to produce a plurality of cross-correlation results for respective repetitive portions in said second set, and a reference selector for selecting one of said repetitive portions in said second set as a reference portion in accordance with its respective cross-correlation results.

Preferably, said reference selector comprises a threshold level comparator for comparing each cross-correlation result with a threshold and which is operable to select as said reference portion a repetitive portion having a highest number of respective cross-correlation results exceeding said threshold.

Preferably, the device further comprises a summation unit for summing cross-correlation results of respective repetitive portions and which reference selector is operable to select as a reference portion a repetitive portion having a highest sum of respective cross-correlation results.

Preferably, said reference selector comprises:

a threshold level comparator for comparing each cross-correlation result with a threshold, and a summation unit for summing cross-correlation results of respective repetitive portions exceeding said threshold, and which reference selector is operable to select as a reference portion a repetitive portion having a highest sum of respective cross-correlation results.

According to a third aspect of the present invention there is provided a waveform frequency component alignment device for aligning first frequency components of waveforms having first frequency and second frequency components, the device comprising:

band pass filters for extracting, respective first and second frequency components of said waveform, a first frequency component aligner for determining a first frequency alignment point of a current waveform with another waveform based on respective first frequency components, and a second frequency aligner for aligning said second frequency components of said respective waveforms based on said first frequency alignment point.

Preferably, said other waveform is a running average of preceding waveforms.

Preferably, said first frequency component aligner further comprises a cross-correlator for cross-correlating a current waveform with said other waveform at a plurality of successive alignments and for determining said first frequency alignment point on the basis of a one of said successive alignments giving a maximum cross-correlation.

Preferably, said first frequency component aligner further comprises an interpolator for interpolating between said cross-correlations at said successive alignments to determine a sub-sample accuracy alignment point between said successive alignments.

According to a fourth aspect of the present invention there is provided a device for analyzing high frequency components of ECG signals, comprising a data extractor for extracting said high frequency components and a data analyzer for determining, from a change over time in at least a part of said high frequency component, whether said ECG signal contains an indication of the presence of ischermia.

Preferably, said at least a part of said ECG signal is a QRS complex.

Preferably, said change over time is a fall in the energy level of succeeding QRS complexes.

Preferably, said change over time is a fall in a cross-correlation value of succeeding QRS complexes.

Preferably, said data extractor comprises a waveform averager for performing iterative averaging over successive ones of said high frequency components to obtain a reduced noise version of said components.

Preferably, the device further comprises a selector for passing to said waveform averager only those ones of said successive components which exceed a threshold cross-correlation with a reference component.

According to a fifth aspect of the present invention there is provided a method for reducing noise in signals having successive substantially repetitive portions, comprising:

superimposing one by one weightwise in iterative steps weighted instances of at least some of said successive substantially repetitive portions, forming a running average of said portions, determining a noise level in said running average, and ending said iterative steps when said noise level reaches a predetermined level, thereby to produce an average of said substantially repetitive portions having reduced noise.

The method preferably further comprises a step of aligning at least some of said substantially repetitive portions one with another, Preferably, said signal comprises first frequency and second frequency components and said step of aligning comprises substeps of extracting said respective first and second frequency components, using said first frequency components to locate an alignment point in each of successive portions, and using said alignment point to align said second frequency components of each of said successive portions.

Preferably, said step of ending said iterative steps further comprises ending when said repetitive portions are exhausted.

Preferably, said step of ending said iterative steps further comprises ending when said running average reaches a preset maximum of included repetitive portions.

The method preferably further comprises the step of selecting repetitive portions for passing to said iterative averager, the step of repetitive portion selecting comprising substeps of:

storing a reference portion,

Computing the cross correlation between a current repetitive portion and said reference portion, comparing a result of said cross-correlation with a predetermined threshold to produce a comparison output, and passing said current repetitive portion for iterative averaging in accordance with said comparison output.

The method preferably further comprises the step of determining as a reference portion any one of a group comprising a first repetitive portion of a current length of said signal, a final result of a running average of a previous set of iterations and a prior determined typical wave.

Preferably, said step of selecting comprises the further substep of dynamically changing between members of said group over the course of a set of iterations.

Preferably, said step of selecting further comprises dynamically updating said reference portion during the course of a set of iterations.

The method preferably further comprises a step of determining a reference portion by:

storing a first set of repetitive portions from said signal, storing a second set of repetitive portions from said signal, cross-correlating repetitive portions from said second set in turn with repetitive portions from said first set to produce a plurality of cross-correlation results for respective repetitive portions in said second set, and selecting one of said repetitive portions in said second set as a reference portion in accordance with its respective cross-correlation results.

The method preferably further comprises:

comparing each cross-correlation result with a threshold, and selecting as said reference portion a repetitive portion having a highest number of respective cross-correlation results exceeding said threshold.

Preferably, said step of determining a reference further comprises:

summing cross-correlation results of respective repetitive portions and selecting as a reference portion a repetitive portion having the highest sum of respective cross-correlation results.

Preferably, said step of determining a reference portion further comprises:

comparing each cross-correlation result with a threshold, summing cross-correlation results of respective repetitive portions exceeding said threshold, and selecting as a reference portion a repetitive portion having a highest sum of respective cross-correlation results.

The method preferably further comprises the step of extracting QRS complexes from an ECG signal to provide said repetitive portion.

The method preferably further comprises extracting an RMS energy value from an average of a series of said repetitive portions.

The method preferably further comprises a step of analyzing said RMS energy to detect for the presence of a falloff in said RMS energy value over succeeding averages.

The method preferably further comprises extracting a cross-correlation value from an average of a series of said repetitive portions.

The method preferably further comprises the step of analyzing succeeding ones of said cross correlation value to detect the presence of a falloff in said cross-correlation value over succeeding averages.

Preferably, said alignment step further comprises cross-correlating a current input with said running average at a plurality of successive alignments, and aligning said signal on the basis of an alignment giving a maximum cross-correlation.

The step of alignment preferably further comprises further comprising interpolating between said cross-correlations at successive alignments to determine a high accuracy alignment between said successive alignments.

According to a sixth aspect of the present invention there is provided a method for reducing noise in signals having successive substantially repetitive portions, comprising:

aligning at least some of said substantially repetitive portions one with another, selecting repetitive portions for passing to said iterative averager on the basis of a comparison with a reference portion, and superimposing and averaging said aligned, selected portions to produce a running average thereof.

The method preferably further comprises a step of selecting from said repetitive portions for passing to said iterative averager, the step of selecting comprising substeps of:

storing a reference portion, carrying out a cross correlation between a current repetitive portion and said reference portion, comparing a result of said cross-correlation with a predetermined threshold to produce a comparison output, and passing said current repetitive portion to said iterative averager in accordance with said comparison output.

The method preferably further comprises the step of selecting as a reference portion any one of a group comprising a first repetitive portion of a current length of said signal, a final result of a running average of a previous set of iterations and a prior determined typical wave.

Preferably, said step of selecting a reference portion includes a substep of dynamically change between members of said group over the course of a set of iterations.

Preferably, said step of selecting a reference portion includes dynamically updating said reference portion during the course of a set of iterations.

The method preferably further comprises a step of determining a reference point, said step comprising, storing a first set of repetitive portions from said signal, storing a second set of repetitive portions from said signal, cross-correlating repetitive portions from said second set in turn with repetitive portions from said first set to produce a plurality of cross-correlation results for respective repetitive portions in said second set, and selecting one of said repetitive portions in said second set as a reference portion in accordance with its respective cross-correlation results.

The method preferably further comprises the further steps of:

comparing each cross-correlation result with a threshold, and selecting as said reference portion a repetitive portion having a highest number of respective cross-correlation results exceeding said threshold.

The method preferably further comprises the further steps of summing cross-correlation results of respective repetitive portions, and selecting as a reference portion a repetitive portion having the highest sum of respective cross-correlation results.

The method preferably comprises the further steps of:

comparing each cross-correlation result with a threshold, summing cross-correlation results of respective repetitive portions exceeding said threshold, and selecting as a reference portion a repetitive portion having a highest sum of respective cross-correlation results.

According to a seventh aspect of the present invention there is provided a method of aligning waveforms having first and second frequency components, said second frequency components being more subject to noise than said first frequency components, the method comprising:

extracting respective first and second frequency components of said waveform, determining an alignment point of a current waveform with another waveform based on respective first frequency components, and aligning said second frequency components of said respective waveforms based on said alignment point Preferably, said other waveform is a running average of preceding waveforms.

The method preferably further comprises the further steps of:

cross-correlating a current waveform with said other waveform at a plurality of successive alignments, and determining said alignment point on the basis of a one of said successive alignments giving a maximum cross-correlation.

The method preferably comprises the further step of interpolating between said cross-correlations at said successive alignments to obtain a sub-sample alignment point.

According to an eighth aspect of the present invention there is provided a method for analyzing high frequency components of ECG signals, comprising the steps of:

extracting said high frequency components and determining, from a change over time in at least a part of said high frequency component, whether said ECG signal contains an indication of the presence of ischemia.

Preferably, said at least a part of said ECG signal is at least part of a QRS complex.

Preferably, said change over time is a fall in an RMS energy level of succeeding QRS complexes.

Preferably, said change over time is a fall in a cross-correlation value of succeeding QRS complexes.

The method preferably further comprises the further step of performing iterative averaging over successive ones of said high frequency components to obtain a reduced noise version of said components.

The method preferably further comprises a selection step of comparing successive waveforms with a reference component and selecting only those ones of said successive waveforms which exceed a threshold cross-correlation level with said reference component for said step of iterative averaging.

According to a ninth aspect of the present invention there is provided a method of obtaining an indication of ischemia in a patient using an ECG signal therefrom, the method comprising:

extracting an ECG signal over a duration, extracting from said ECG signal a series of at least partial QRS complexes over said duration, extracting high frequency components of said QRS complexes, analyzing said high frequency components over said duration for at least one of a predetermined quality, and inferring from said predetermined quality an indication of ischemia.

Preferably, said predetermined quality is a falloff in a cross-correlation level with a reference component.

Preferably, said predetermined quality is a falloff in the energy level of said component.

Preferably, said step of extracting said high frequency components comprises carrying out iterative steps of averaging over preselected ones of successive components to reduce noise Preferably, said step of extracting an ECG signal is carried out over a duration of a stress test comprising placing the patient in at least one of a group of phases comprising rest, stress, and recovery from stress.

Preferably, said step of extracting an ECG signal is carried out over a duration of an event being any one of a group comprising: acute myocardial ischemia, other forms of heart failure, coronary occlusion, and coronary angioplasty, said duration being any one of a group comprising before, during and after said event.

Preferably, said ECG signal is masked by another ECG signal.

According to a tenth aspect of the presetninvention there is provided a method of producing a noise reduced waveform from a series of substantially similar repeated waveforms having superimposed noise, the method comprising:

selecting waveforms having a highest cross-correlation with a preselected reference waveform, and carrying out iterative averaging steps using said selected waveforms.

The method preferably further comprises the step of ending said iterative averaging when a signal to noise ratio of a result of said iterative averaging has a level below a predetermined threshold.

BRIEF DESCRIPTION OF THE DRAWINGS

For a better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DESCRIPTION OF THE PREFERRED EMBODIMENTS

Figure 1:
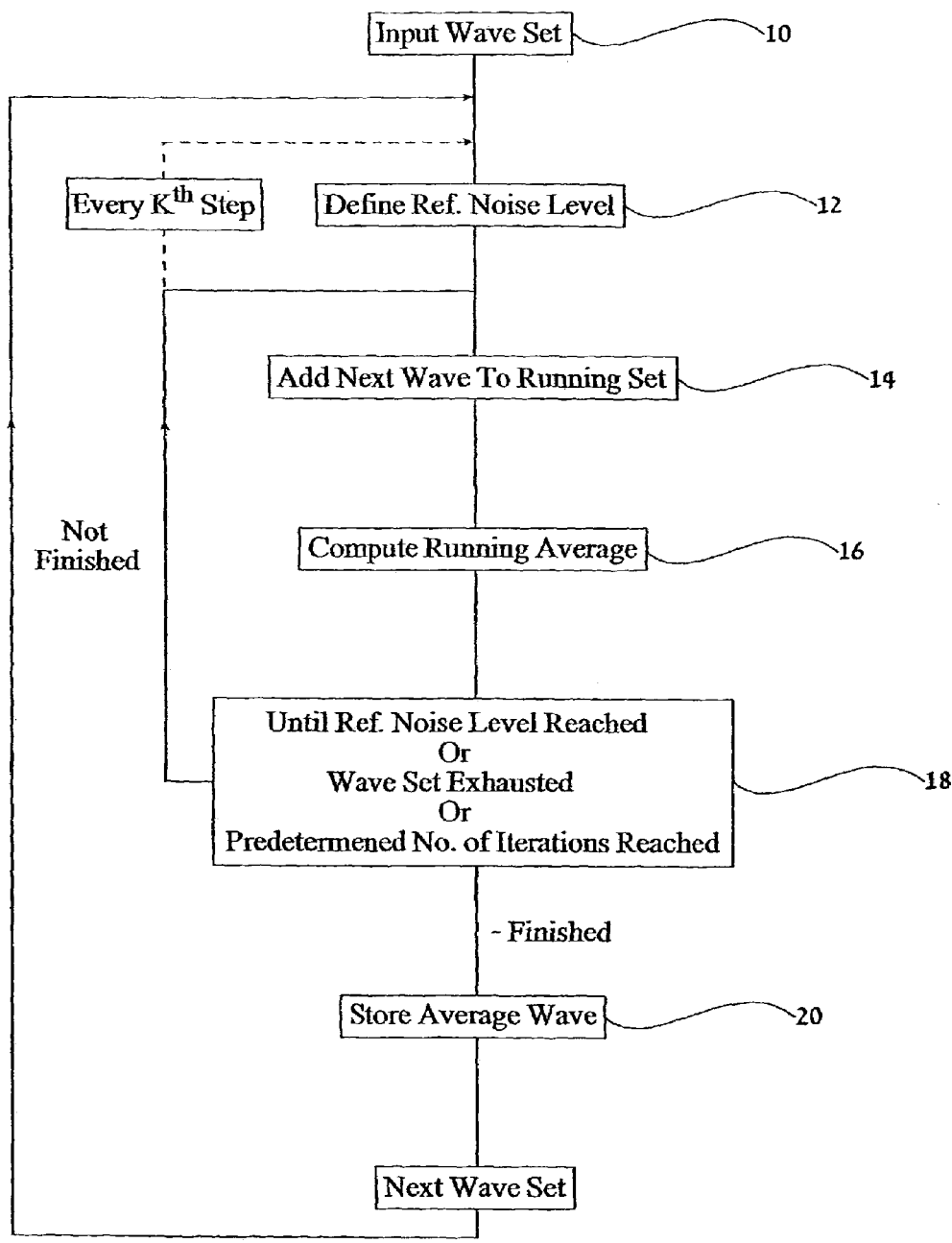
FIG. 1 is a generalized flow diagram showing a method of signal averaging according to a first embodiment of the present invention.

Before explaining at least one embodiment of the invention in detail, it is to be understood that the invention is not limited in its application to the details of construction and the arrangement of the components set forth in the following description or illustrated in the drawings. The invention is applicable to other embodiments and of being practiced or carried out in various ways Also, it is to be understood that the phraseology and terminology employed herein is for the purpose of description and should not be regarded as limiting.

In this specification, terminology is used in accordance with the following definitions:

1. "signal" refers to an entire length of periodic or semi-periodic input
2. "segment" indicates an arbitrary part of the signal (usually, but not necessarily, a continuous part of the signal).
3. "wave" means a segment consisting of a single occurrence of the periodic part of the signal.
4. calculable or measurable variables are herein defined to be equivalent to each other if they are substantially proportional to each other.

To simplify the following description it is assumed that, unless explicitly stated otherwise, the adaptive averaging procedure takes as its input:

a digitized signal, a set of waves extracted from that signal and aligned using any method known in the art, and for each wave, pointers indicating its correct beginning and end within the signal. The skilled person will appreciate that, in order to arrange such inputs, a certain amount of pre-processing using known systems will be required.

The output of the procedure is an array of waves, obtained from the original set of waves by applying noise reduction to the set. Preferably, the output for each waveset is an array of "cleaned" waves. I.e. whenever the averaged wave resulting from noise reduction reaches a satisfactory noise level the algorithm does not stop but rather restarts the same procedure, either with the next wave in the same waveset or with a new waveset, as appropriate in the circumstances.

The noise reduction procedure of the preferred embodiments is based on averaging sets of succeeding waves in an iterative process. At each iteration of the adaptive averaging procedure a new wave is incorporated into a set of waves created during the previous stages and an average is calculated over the modified set. As will be described below, an alternative embodiment stores at each iteration only the averaged wave, and then obtains a new averaged wave using a weighted averaging wherein, at the $n^{th}$ iteration the averaged wave has weight (n−1) and the new wave has weight 1.

Unlike the averaging procedure suggested in the above mentioned prior art patent, in which each new wave is averaged with the wave produced in the preceding step, embodiments of the present invention are able, at least conceptually, to reduce the signal to noise ratio to any desired level.

A preferred feature of the present embodiments is that they permit a user to define a target signal to noise ratio. Such a target may be either constant, or may dynamically change according to a function, supplied by the user, taking as arguments such parameters as the local noise level, the local signal amplitude etc. The use of a selected target level is advantageous in that it provides assurance that as soon as the selected target signal to noise ratio has been reached no further processing takes place, thus minimizing attenuating effects caused by surplus noise reduction steps.

Thus, whenever the required signal to noise ratio level is attained, the current averaged wave is stored in an array of results, and the procedure is repeated with the next wave in the queue. If the target level is not reached within a predetermined number of iterations, the procedure stores the result after the predetermined number of iterations and moves on to the next wave or waveset in a new noise reduction procedure as described above.

In order to improve the averaging procedure and reduce attenuation in the signal produced by the averaging, waves with exceedingly high noise level are preferably identified so that they are not incorporated into the average. Therefore, in a preferred embodiment, a reference wave is used in order to rate the waves—for example using the cross correlation coefficient between the candidate input wave and the reference wave—such that only those waves whose rating is above a predetermined level are included in the average.

Reference is now made to FIG. 1, which is a generalized flow diagram of a signal averaging procedure according to a first preferred embodiment of the present invention, for enhancing a signal to noise level of the signal to a predetermined level. The predetermined level may be set as a function of a current noise level in the signal or in any other way. It is desirable that the predetermined level is not too exacting, as excessive noise reduction tends to harm fine information structures in the signal. On the other hand the level should be sufficiently high to render the signal intelligible for analysis purposes later on. In FIG. 1, in a first step 10, an input wave set is received from an external source and stored in a buffer or other storage means. The input wave set may be a segment of a signal and may comprise a plurality of repeated portions (waves). This step is followed by a reference definition step 12 in which a reference noise level is defined, as will be explained in greater detail below, and this is followed by a step 14 of taking a next wave of the set obtained in step 10. Preferably, the "next wave" is the first wave—in temporal order—not yet incorporated to the running set.

The next wave is judged against a series of criteria as will be described in more detail below and, if it is found to qualify, is added to a running set of waves taken from the current input waveset.

In a step 16, an average is calculated of the running set of waves, as updated by the next wave in step 14. In the case of the first qualifying wave in the set the wave itself constitutes the average. Generally, even though a waveform may vary over time, waves that are close to one another vary very little and thus averaging such closely related waves is an effective method of removing noise whilst retaining as much as possible of the essential structure of the waveform.

The step of averaging is repeated by taking succeeding waves in the waveset, and thus carrying out an iteration of steps 14, and 16 until one of the following events occur:

1) a reference low noise threshold is reached,
2) the input waveset is exhausted of all waves, or
3) a predetermined number of iterations has been reached.

The reference low noise threshold is preferably calculated based on the reference noise level defined in step 12 above.

The continuation or ending of the iterative process is illustrated by process step 18, and such control of the iterative process is preferred because it provides a means for ending the noise reduction process before waveform structure is adversely effected. To this end the reference noise threshold level and the number of iterations are preferably both set to optimize for later analysis of the waveform, which demands minimal noise but maximal surviving waveform structure.

At the end of the iteration series of the current waveform set, in step 20, the resulting average waves are stored for later analysis. The original waves that have already been processed from the current waveset set and the running waveset may now be deleted if no longer required.

If the current waveset is not exhausted, the running set is deleted, a next wave is chosen, and the process continues from step 14. The choice of the next wave may be the first wave in the temporally arranged waveset that has not been processed. Another way of choosing the next wave may be by choosing, for example the second wave in the running set. Such a choice preferably ensures that the new average is very close to the previous one, resulting in a much smoother change in the array of averaged waves. When the current waveset is exhausted, a new waveset is chosen for iterative analysis, and the that different waves having broadly the same waveform may be aligned. Details of the process of introducing alignment markers will be discussed in greater detail below. In step 42 the next wave is aligned, using the alignment marker, with the waves in the running set of extracted waves. The aligned wave is now added to the set in step 44 and, because all the waves are aligned it is possible to compute a new average over all the waves in the running set in step 46.

Figure 2:
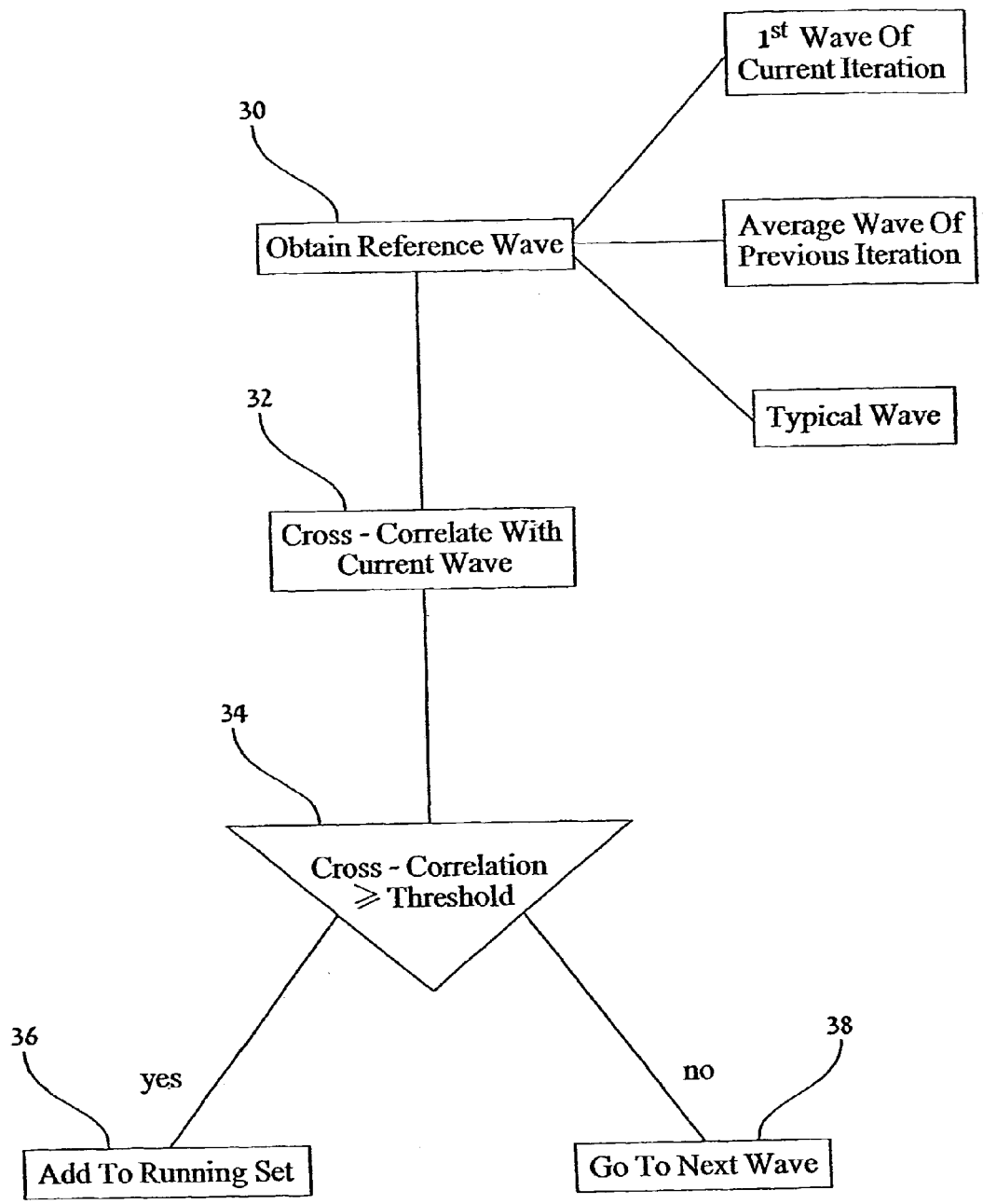
FIG. 2 is a generalized flow diagram showing in greater detail the stage of selecting an individual wave by thresholding, according to the embodiment of FIG. 1.
Figure 3:
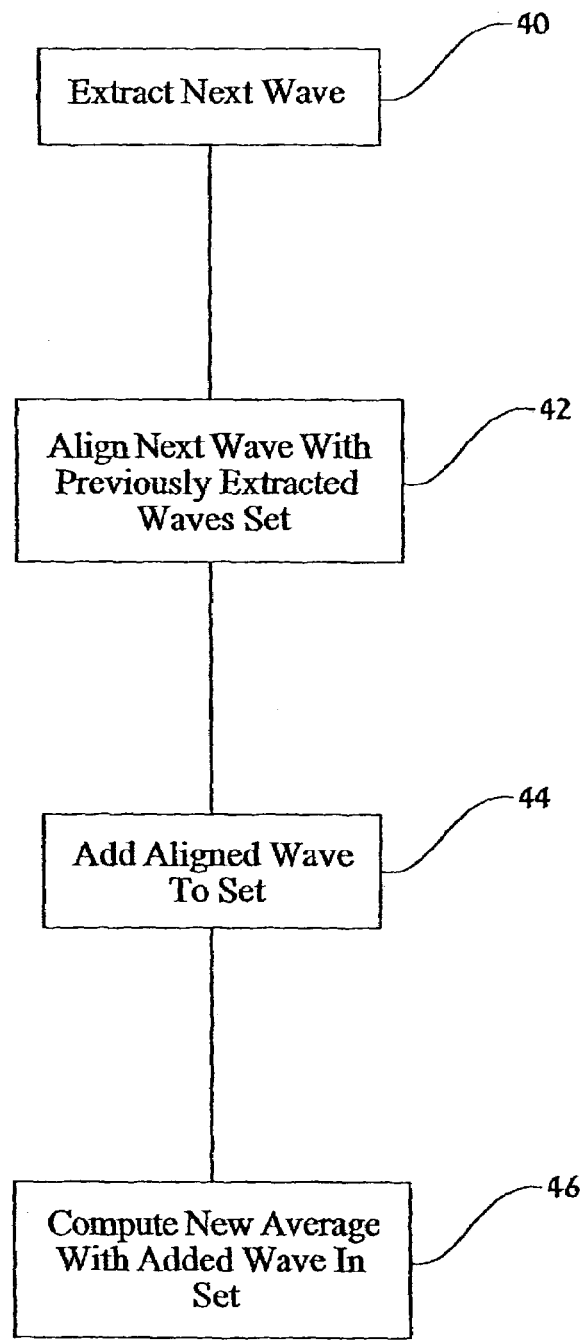
FIG. 3 is a generalized diagram showing how a newly extracted wave is aligned with an existing set before averaging according to the embodiment of FIG. 1.
Figure 4:
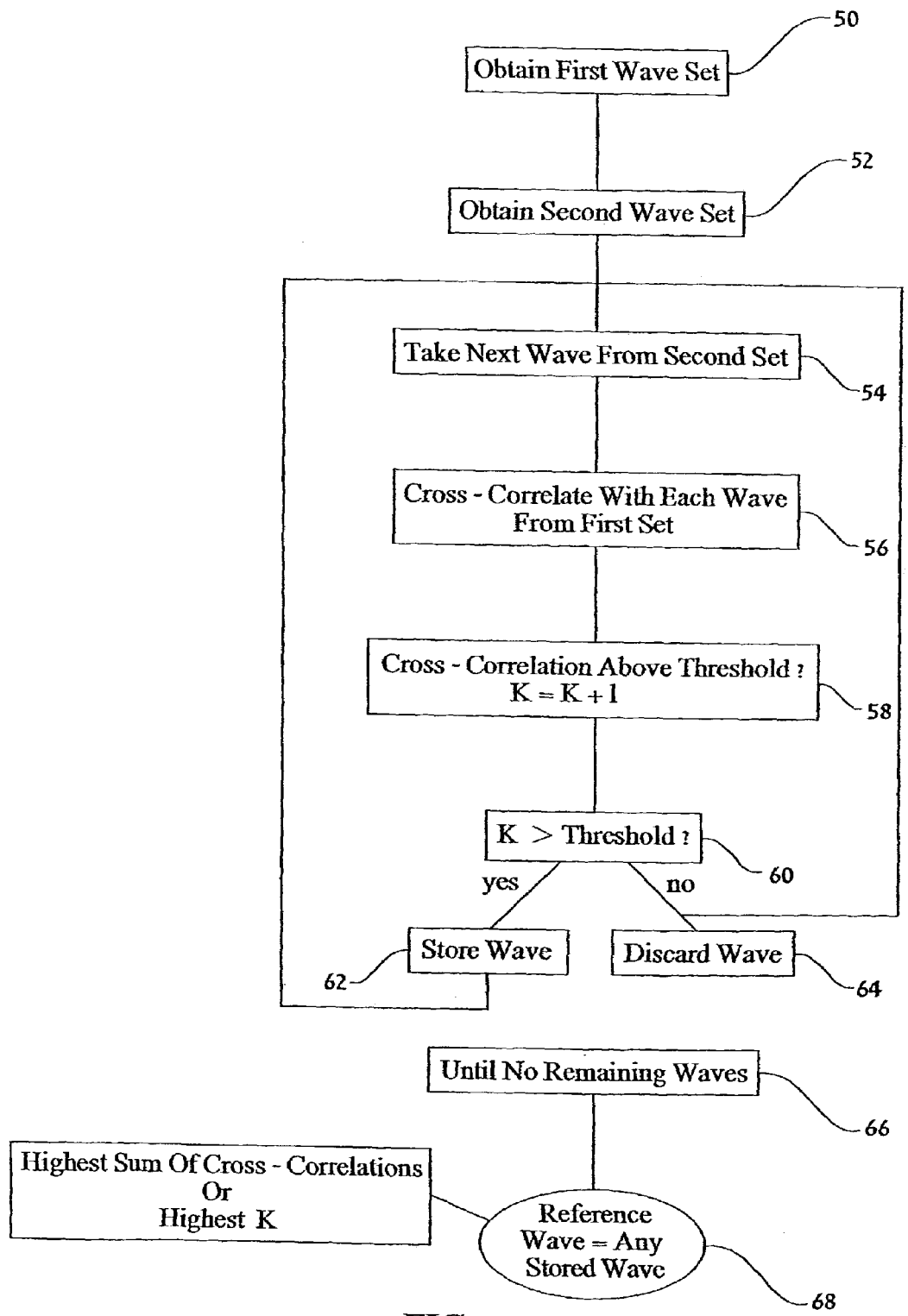
FIG. 4 is a generalized diagram showing a preferred method of obtaining a reference wave for use in the embodiment of FIG. 1.

Referring back to FIG. 2, a number of possibilities were mentioned for obtaining a reference wave and it has been shown how a preferred embodiment uses such a reference wave to decide whether to accept a next wave into the running set. Reference is now made to FIG. 4 which is a generalized flow diagram showing a preferred embodiment for obtaining a reference wave based on individual waves from two wavesets. In FIG. 4 a first waveset is obtained from an input signal and individual waves are stored in a step 50. Then, in a step 52 a second set of waves are obtained and stored in the same way. In step 54, successive waves are taken from the second set and in a step 56 cross-correlation between each of the waves in the second set and each of the waves in the first set is computed to produce a cross-correlation result. Each cross-correlation result is then tested against a threshold level in step 58 and then for each wave in the second set a value k is assigned giving the number of waves in the first set with which the respectively computed cross-correlation coefficient exceeded the threshold. In step 60 the k value for each individual wave from the second set is tested against a threshold, and provided that k exceeds a predetermined threshold, the wave is added to a stored waveset in step 62. Otherwise the wave is discarded in step 64.

The procedure preferably continues until all of the waves in the second set have been processed, step 66, and then one of the waves of the stored waveset is selected as the reference wave. There are a number of possibilities for selecting a reference wave from the stored waveset that may be considered by the skilled person. One preferred possibility is to take the wave having the highest sum of cross-correlations and another preferred possibility is to select the wave having the highest k value as a reference value.

There is thus described, in FIGS. 1 to 4, a system of adaptive averaging which allows an input signal comprising a repetitive waveform to be segmented and for a clean version of the waveform to be produced for later analysis. The system is useful for any input signal having a repetitive portion and unwanted noise and is particularly useful when analysis is dependent on careful preservation of fine structural portions of the signal.

Figure 5:
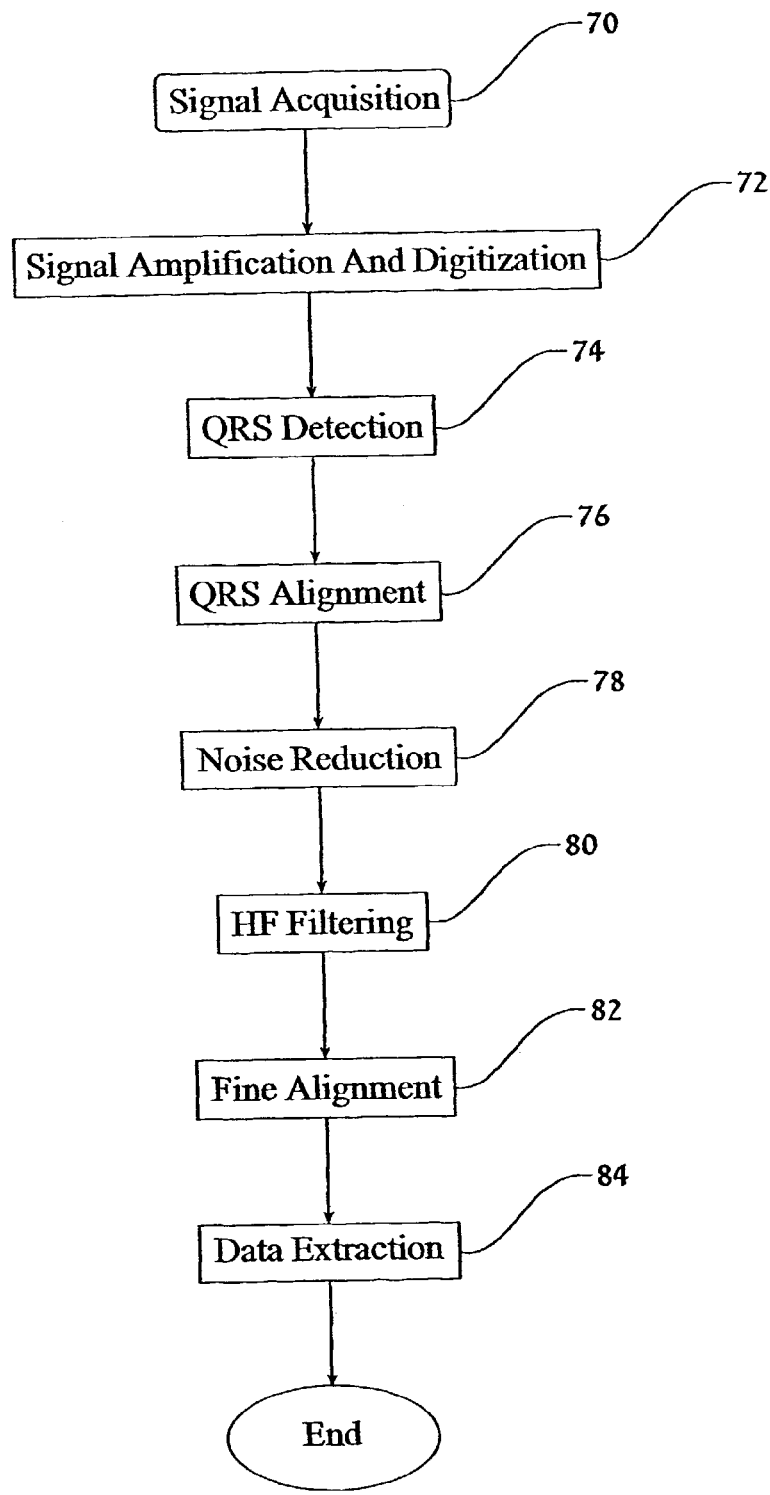
FIG. 5 is a generalized block diagram showing the application of the embodiment of FIG. 1 to a system for extracting information from an ECG signal.

Reference is now made to FIG. 5, which is a simplified block diagram of a system for carrying out adaptive averaging prior to analysis of an ECG signal. The system comprises a signal acquisition unit 70, which obtains signals from an input source, in this example, an ECG signal.

The signal is typically an analogue signal containing fine structure, as will be described in further detail below and is generally initially mixed with noise. As will be discussed in more detail below, the noise forms a higher proportion of the overall input at frequency bands of interest, such that other frequency parts of the signal are generally usable directly, but the signal at the desired frequency parts generally requires noise reduction. However, important information carried in parts of the signal in the frequency band of interest is liable to be distorted or lost by conventional noise reduction techniques.

A signal amplification and digitization unit, 72, processes the signal so that it can be supplied for digital signal processing. The QRS complex part of the signal is then detected by a QRS detection unit 74 and then an alignment unit 76 detects individual waves and marks corresponding portions of the waves for subsequent alignment.

The alignment unit is connected in series to noise reduction unit 78, HF filtering unit 80 and fine alignment unit 82 respectively, the functions of which will be discussed below. Finally a data extraction unit 84 extracts averaged waveforms for subsequent data analysis.

In order to understand the embodiment of FIG. 5 in greater detail, the following preliminary remarks are made regarding analysis of HF ECG. As has been shown by Abboud et al., an ischemic condition of the heart is highly correlated with significant decrease of the HF ECG signal of the QRS complex. Further studies by Beker et al. (see above) have shown that a decrease of the HF ECG of the QRS complex during exercise test could serve as diagnostic aid for early detection of cardio-vascular infarction, in a way that is much more sensitive than the standard ECG signal.

Enlarging on what was stated above concerning the need for noise reduction, the HF ECG signal is typically weaker and thus harder to detect in a meaningful manner than the standard ECG and, therefore, cannot be usefully dealt with before significantly improving the signal to noise ratio. However, even during a comparatively long test such as an exercise test (typically 10–20 min. long) the decrease in the HF ECG level may quite often be observed only in relatively short intervals (2–3 min.). Thus a noise reduction method that requires averaging large number of waves can significantly attenuate the effect for which it was employed, which means that the decrease in the HF ECG signal is barely noticeable in the noise reduced signal.

From the above preliminary remarks it is clear that the analysis of HF ECG preferably requires a noise reduction method that will not abolish transient changes, since the transient changes are of great diagnostic significance in that signal. The adaptive averaging method of the embodiments described above in respect of FIGS. 1–4 preferably allows a significant reduction in the noise level of the HF ECG, with a considerably weaker attenuation effect on phenomena, particularly transient phenomena, due to changes in the signal itself. FIG. 5 illustrates the general outlines of a specific embodiment intended for the processing of an HF ECG signal in such a way as to remove noise but to retain transient information.

The block diagram of FIG. 5 preferably enables a procedure which permits analysis of the HF signal of the QRS complex. Thus, in the following may be aligned and then aligning them. In order to perform an alignment procedure it is preferable that the complexes are free of any DC components. Preferably, any such DC components are removed at least by the time that QRS component detection has been completed, either by rejecting the DC of the raw signal before performing the detection and extraction of the waves, or by performing QRS detection using the raw signal but extracting the waves themselves from a signal that has already been high-pass-filtered.

It is noted that from a practical point of view, the alignment unit 76 and the noise reduction unit 78 of the system of FIG. 5 may be merged and implemented as a single unit, although from the conceptual viewpoint they are distinct. Thus, in the present discussion units 76 and 78 will be described separately, although in practice the skilled person would probably see fit to implement them as a single unit carrying out both functions together.

In order to simply the implementation of the alignment unit 76, it is preferable to assume that the waves extracted from the signal around each maximum point of the cross correlation function share substantially the same length. However, such an assumption is very much dependent on the circumstances of individual embodiments, in particular on different data extraction methods, and the procedure used by the alignment unit is preferably modified to suit any extraction method chosen by the user.

As stated above, the HF ECG signal is relatively weak compared with the expected or typical noise level in the signal. Consequently, the cross correlation of a template HF ECG wave with a wave of raw data may be expected to be dominated by noise, resulting in poor alignment results. However, the HF of the QRS complex is considered to correlate effectively with the standard low frequency wave, i.e. alignment of the low frequency signal will automatically give an alignment of the HF signal. As a result, by contrast with the method of U.S. Pat. No. 4,732,158, discussed above, alignment is preferably carried out using the low frequency wave. The low frequency wave generally has significantly better S/N, and thus HF alignment may effectively be carried out on signals with levels of noise that in fact completely mask the whole HF ECG.

Figure 6:
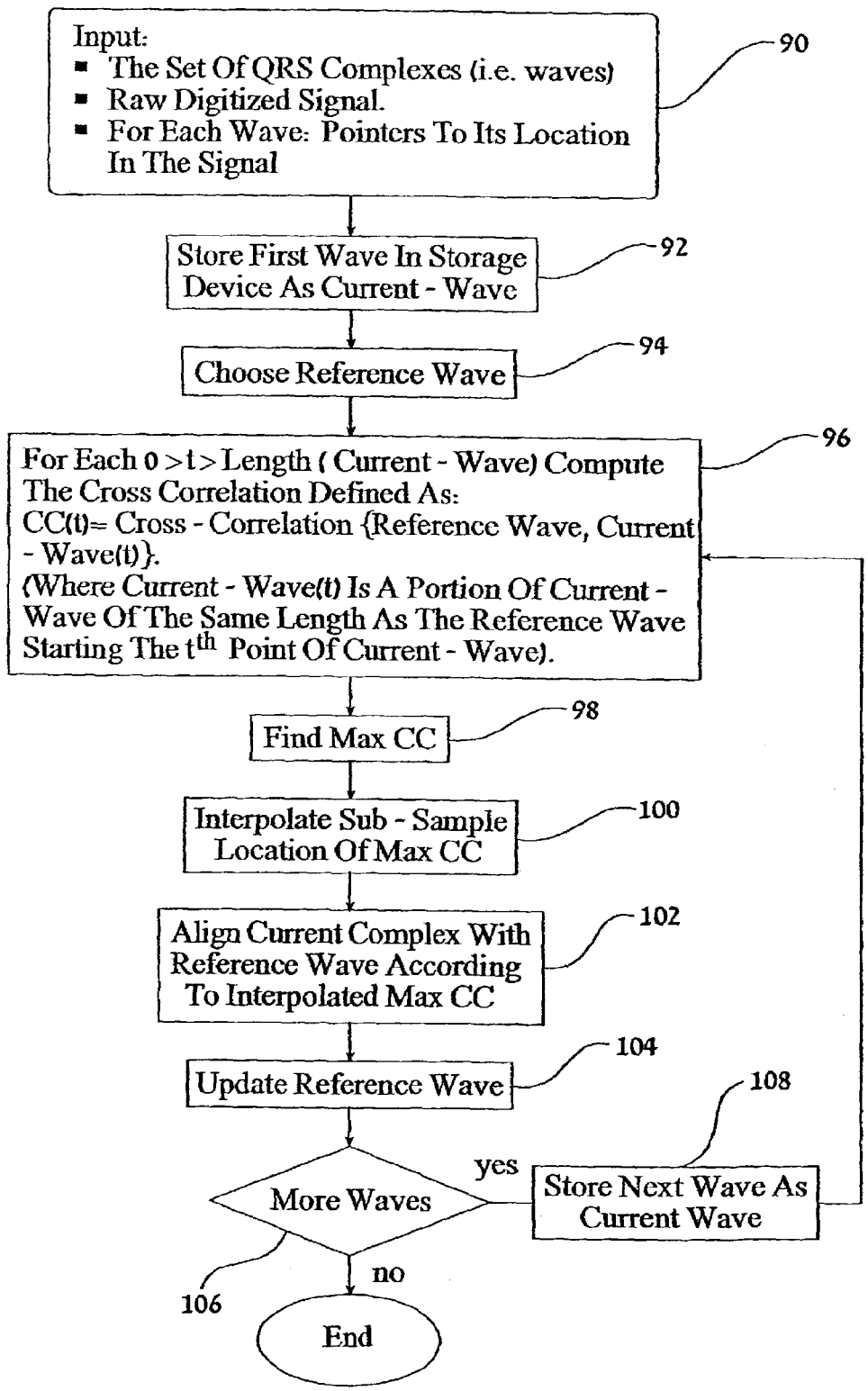
FIG. 6 is a generalized flow diagram illustrating an alignment stage in adaptive averaging of an ECG signal.

Before considering the remaining sections of FIG. 5, reference is first made to FIG. 6, which is a generalized flow diagram describing a preferred operation of the QRS alignment unit 76 of FIG. 5.

In the process of FIG. 6, a current set of QRS complexes (waves) is received as input in a first stage 90, preferably together with the raw digitized signal itself and pointers for each complex to show its location in the raw digitized signal.

In a stage 92, a first wave is selected. In a stage 94, a reference wave is selected, preferably as has already been described in respect of FIGS. 1 to 4. Then, in a stage 96, the selected wave is shifted against the reference wave and a series of cross-correlations are calculated for different relative positions of the two waves. In a stage 98 a position corresponding to the maximum cross-correlation is then determined as a first approximation of the correct alignment of the selected wave. A more accurate location is then preferably obtained in a stage 100 by interpolation, as will be described in more detail below. In a step 102, the selected complex is aligned with the reference wave in accordance with the interpolation result of step 100, and this is preferably followed by a step 104 of updating of the reference wave. If there are more waves (query step 106) then a new wave is loaded as the selected wave (step 108) and cross-correlation/alignment is repeated.

Particular emphasis in FIG. 6 is laid on the steps choice of and updating of the reference wave (94 and 104) and the interpolation of the sub-sample location of the alignment or fiducial point (step 100).

The reference wave is preferably used to define the fiducial point with which alignment is preferably made. Each selected wave is aligned, using the fiducial point, with the reference wave, and by assuming transitivity, alignment of the whole set of waves is thus achieved. In order for transitivity to apply, the reference wave is preferably selected and updated in such a way as to ensure that alignment responds to changes of the wave with time (such a change may for example be indicative of development of a Bundle Branch Block during the exercise test) but, on the other hand does not respond to local or transient changes (such as Premature Ventricular Contractions, should these not have been taken care of earlier by previous processing of the signal).

As discussed in detail above, there are many methods for the choice of the reference wave that may be used in step 94. Among these methods the following are preferred:
1. The first wave in the current iteration of the process.
2. A typical wave obtained during previous measurements or synthetically created according to theory.
3. The method outlined above in respect of FIG. 4, namely obtaining a set of aligned waves corresponding to a second signal (typically which is similar to the first signal) and executing the following steps:
   a. Store k (a predetermined number) waves from that set.
   b. For each of the stored waves:
      i. Calculate the cross-correlation of each of the k waves with n (a predetermined number) successive waves of the first signal.
      ii. For each of the k waves of the first set determine the number, $N_i$ ($0 \leq i \leq k$), of waves out of the n waves of the second set with which its cross-correlation coefficient (as calculated in step i) exceeds a predetermined threshold.
      iii. From the first set of k waves create a set of "candidates" containing all those waves with $N_i$ (the number determined in stage ii) above a predetermined value (depending on n).
   c. If the set of "candidates" created in stage iii is empty, reiterate the process with a new set of n waves (as in stage ii).
   d. If the set of candidates created in stage iii is not empty, choose one of the candidates of that set. The choice of the reference wave from the candidate set may be made as follows:
      i. A wave for which the sum of the calculated cross-correlation values is maximal; or
      ii. A wave having a maximal number of cross-correlation values above the predetermined threshold.

For step 104, the update of the reference wave, a few approaches may be considered, for example:
1. Continuously updating the reference wave.
2. Updating the reference wave whenever a predetermined number of waves have been aligned since the last update.
3. Updating the reference wave when the current reference wave gives poor cross correlation coefficients with a predetermined number of consecutive waves.

The update itself may be carried out in numerous ways, including:
1. Repeating the procedure outlined above for the choice of a reference wave each time an update is required.
2. Using a wave obtained by averaging over the last n waves aligned in the process, where n is a predetermined number.

Step 100 of the process comprises interpolation of a sub-sample location for the fiducial point. Consider, for example, the analysis of the 150–300 Hz band of the QRS complex. An A/D converter with a sampling rate of 1 KHz assures that no information in the desired band is lost. However the accuracy of an A/D converter of 1 KHz in the time domain is of 1 ms, which does not permit sufficiently accurate alignment (at 250 Hz an error of 1 ms corresponds to a phase shift of 90°).

For each wave, the fiducial point, used as the basis for alignment, is the point giving maximum cross correlation of the selected wave with the reference wave (steps 96 and 98). Thus, obtaining a sub-sample accuracy ('sub-sample accuracy' meaning accuracy in excess of the sampling rate of the A/D converter) for the fiducial point amounts to interpolating the exact location of the maximum of the cross correlation function CC(t) defined in step 96. This can be effectively achieved as the cross correlation function may be considered a very smooth function. Thus relatively incomplete data may be analytically interpolated by any method known in the art to give an exact location of the maximum beyond the sampling resolution. A simple method for the interpolation of the exact location of the maximum of the cross-correlation function involves approximating it to a polynomial of degree k (depending on the desired accuracy) using the values of CC(t) at, say, 2 k points about the maximum indicated by stage 98. In general the result of interpolation stage 100 is given as a fraction corresponding to an abstract point between two given points of the digitized signal. Thus, in order to correctly perform the alignment the whole wave must be shifted by that fraction (i.e. the correct values of the signal at intermediate points (n+fraction) has to be calculated). This can be easily achieved (e.g. by using an interpolation filter) as the sampling rate of the signal is assumed to be adequate.

The alignment algorithm of FIG. 6 thus preferably results in a set of aligned QRS complexes or waves. The noise reduction stage 78 of FIG. 5, may thus receive inputs as follows:
1. The set of aligned waves.
2. The raw digitized signal.
3. For each wave: pointers to its location in the signal.

Figure 7:
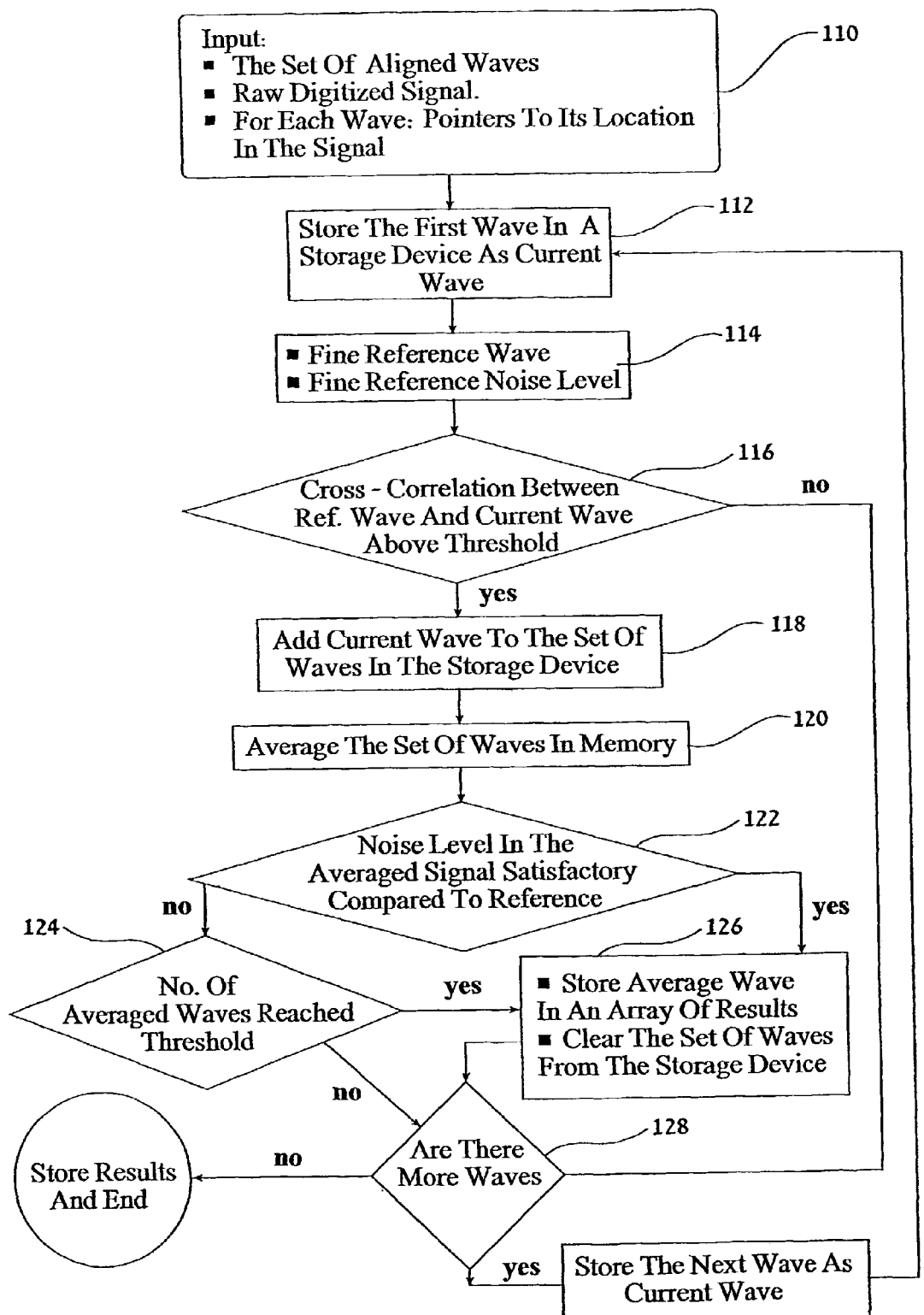
FIG. 7 is a generalized flow diagram showing noise reduction in a wave set extracted from a signal such as an ECG signal.

Reference is now made to FIG. 7, which is a simplified flow diagram showing in more detail the noise reduction stage 78 of FIG. 5.

In FIG. 7, a first step 110 indicates receipt of the above listed inputs. In step 112 a first wave is selected for processing. In step 114, a reference wave and a reference noise level are selected. In a step 116, the cross-correlation function of the aligned selected wave with the preselected reference wave (preferably still available from the alignment stage) is compared with a threshold. Provided that the result exceeds the threshold the selected wave is then added in step 118 to the running set. If the threshold is not exceeded then the selected wave is discarded and the procedure moves on to the next wave. If the selected wave was added then the running wave set is averaged in step 120 and then the noise level of the newly averaged wave is compared to a reference in a step 122. Preferably, as will be discussed in more detail below, the step of discarding waves with low cross-correlation to the reference wave ensures that noise is not added to the running set prior to averaging.

Then, in decision stages 122, 124 and 126, the process ends the noise reduction stage if the noise level has dropped below the reference level, or if the number of waves averaged has reached a predetermined threshold, or there are no more waves left. Otherwise the process is repeated with the next wave in the set.

Particular emphasis in FIG. 7 is laid on the steps of the definition of the reference wave and the reference noise level (step 114) and the termination points of each iteration of the algorithm (steps 122, 124, 126 and 128).

The choice of the reference wave in the procedure of FIG. 7 may be made in the same way as in the procedure of FIG. 6, and in an implementation combining the two procedures into one, it may be convenient to use the same reference wave.

In the procedure of FIG. 7 the reference wave is preferably used to identify waves with comparatively high levels of noise for exclusion from the running set. Waves whose cross-correlation coefficient with the reference wave is not high enough to satisfy a predetermined threshold are not incorporated into the average wave in step 118 but are instead discarded, thus reducing the number of waves used in the averaging process.

The reference noise level is needed to calculate the S/N ratio in the raw signal and to assess an expected amount of averaging needed to reach the target S/N. Alternatively, the reference noise level may be used to determine a target S/N that is deemed sufficient for the analysis of the signal. The target S/N is preferably a level that may be reached by averaging over a sufficiently small number of waves such that transient changes, which may be of importance in the subsequent analysis, will not be attenuated.

In either of the above cases the reference noise level is preferably regarded as an input for a function, preferably supplied by the user, that defines when the S/N level of the averaged signal has reached a satisfactory level (step 122) and that also defines a threshold on the maximal size of the set of averaged waves (step 124).

Whichever of the two possibilities is selected for use of the reference noise level as described above, the reference noise level is preferably calculated from a signal to noise analysis of the raw signal in the following way:

a. Using the pointers of the waves in the current set to indicate correct points of origin of the respective waves in the initial raw signal, and with access to that signal, segments are preferably selected over which the reference noise level is to be computed, as segments in the "neighborhood" of the waves in the set. Alternatively, the noise level may be calculated using any segment of the raw signal.

b. Define a set of "quiet" segments:
  i. If the set of waves does not cover the whole neighborhood of the segment to be considered, (that is, in the given segment there are intervals between some of the waves) preferably choose new segments out of these intervals.
  ii. Alternatively, choose a number of waves from the neighborhood of a segment to be considered. In each wave find an interval during which there is a low signal level, and choose segments for noise analysis from these intervals.
  Regardless of the way the "quiet" segments have been chosen, it is preferable to ensure that the total length of the segments selected for noise analysis surpasses a predetermined threshold.

c. Defining a reference noise level based upon the noise levels of the segments selected in the previous stages. The noise level in each segment, can be defined, for example as the root mean square (RMS) of the signal in that segment.

Each wave not eliminated after step 116, is now preferably incorporated into the running set, that is to say along with all previous waves of the same set which have not been eliminated. At each iteration, the average wave of the updated set is preferably calculated (step 120).

The noise level of the average wave is now calculated in step 122 as described above. Step 122 bears close attention as it ensures that as soon as the desired S/N ratio of the average wave (as determined by the user) has been reached no further averaging of the present set takes place, thereby reducing attenuating effects due to surplus noise reduction. As long as the required S/N has not been attained the algorithm keeps adding new waves to the averaged set, until a threshold number of waves (preferably determined according to a function supplied by the user) is reached. When such a threshold is reached (step 124) iteration on the current waveset is stopped, and a new iteration process starts with the next waveset (segment etc.) in the queue, as discussed with regard to the continuation of the process of FIG. 1 after step 20.

Returning now to FIG. 5, and after the termination of the noise reduction procedure (section 78), preferably the resulting S/N ratio of the averaged wave, in the frequency band of interest, is favorable. Now, in a filter unit 80, the averaged waves are preferably band-pass filtered to leave only the frequency band of interest. The design of the band-pass filter for the processed, noised reduced standard ECG QRS complexes obtained from the previous stages preferably takes into account several parameters including:

1. The locality of the phenomenon in the time domain (that is to say, when looking for a given phenomenon in the QRS complex—either in the standard ECG or the HF ECG—what is the coarsest time resolution in which we may reasonably expect to be able to detect the phenomenon?).

2. The locality of the phenomenon in the frequency domain. It is noted that important phenomena in the HF ECG do not have any trace in the standard ECG. As the energy levels of the ECG signal in the lower band of the spectrum are much higher, the locality of a phenomenon in the frequency domain is defined as the largest frequency range in which the low frequency signal will not conceal it.

Filter parameters selected in accordance with either one of the two considerations above may be mutually exclusive. In practice an optimal filter is selected based on the individual traits of the phenomenon to be dealt with.

It should be stressed that different implementations of the algorithm may call for different filters and different frequency bands. These parameters should preferably be selected in accordance with the requirements of the data analysis in the given case being taken into account.

Although, for the purpose of the alignment procedure it has been assumed above that the HF signal of the QRS complex is highly correlated with the low frequency or standard QRS, local phenomena in the low frequency ECG, which have no trace in the HF ECG (e.g. transient "notches" that appear or disappear during exercise) may cause slight deviations in the alignment of the HF signal. Realignment of the filtered waves (say as in step 102 in FIG. 6, with the band-pass filtered signals as input) will usually eliminate such deviations.

Preferably, an additional stage of noise reduction (not appearing in the diagram of FIG. 5) may be applied to the set of filtered and realigned waves. More precisely, after the first noise reduction procedure (unit 78) has reduced the S/N ratio in the band of interest to a level that makes it possible to align the band-pass filtered waves, a reiteration of the procedure of FIG. 7 may be carried out using the aligned band-pass filtered set of waves as input. Partitioning the noise reduction process into two stages has two main advantages:

1. Reiterating the alignment algorithm with the band-pass filtered waves helps exclude certain extremely noisy or abnormal waves wherein the anomaly is not detectable in the standard, or low frequency ECG signal, (it will be recalled that initial alignment was carried out using the low frequency version of the wave) and
2. As stated above, alignment using band-pass filtered waves gives a better alignment of the HF ECG than that achieved using standard ECG, thus reducing the risk of attenuation, during the averaging procedure, of important data contained in the signal.

It is noted that, in order to implement the system of FIG. 5 using the partitioning of the noise reduction procedure as outlined above, the user may preferably supply the procedure of FIG. 7 with two different noise level targets (as in stage 7 of that algorithm) as follows:

1. A noise level that allows an efficient alignment of the band-pass filtered waves. (The "target noise" for the first iteration), and
2. The desired final noise level, required for the inspection and analysis of the signal. (The "target noise" for the second iteration).

In an alternative embodiment, the fine alignment procedure (using fine alignment unit 81 in FIG. 5) may be dispensed with. In its place, a procedure utilizing the following steps is preferably adopted:

1. Proceed with signal acquisition, signal amplification and digitization, QRS complex detection and QRS complex alignment, thereby to create an array of aligned waves complete with pointers to their correct original location in the raw signal.
2. Use the aligned waves to create an array of waves with relatively low level of noise in the frequency band of interest. This can be done as described above in respect of the noise reduction unit 78 of the system of FIG. 5, or more simply by averaging a predetermined number of consecutive waves in the array.
3. Band-pass filter each of the waves obtained at the previous stage to the desired frequency range to create a set of reference HF waves.
4. Band-pass filter each of the waves obtained by signal acquisition unit 70 to the desired frequency range to form an array of HF waves.
5. Proceed with the alignment and noise reduction procedures of units 76 and 78 in the system of FIG. 5 (as described in FIGS. 6 and 7 respectively) using the set of HF waves created in the previous unit as input and with the array of averaged and band-passed waves from preceding stages or otherwise obtained as reference waves.

The above procedure avoids relying on the low frequency signal for performing alignment, thus bypassing the inaccuracies referred to above requiring a separate fine alignment procedure.

Preferably, each segment selected for examination contains a QRS complex and only one such complex. Thus, the restriction of the alignment procedure to a single wave at a time makes it possible to perform alignment over waves with relatively high S/N ratio. Furthermore, the cross-correlation function of the LF signals (See FIG. 6 above) preferably gives a clear indication as to where in each segment to look for the fiducial point corresponding to that segment.

However, as the S/N ratio in the frequency band of interest is typically much lower than in the standard low frequency part of the ECG signal there may be circumstances in which the S/N in the required frequency band will not permit alignment in that band even using the above-described procedure, whilst in the standard ECG, an acceptable alignment could yet be achieved. Thus in order to implement the above-described modified procedure some assumption regarding the S/N in the band of interest is preferably made to give a yardstick to determine whether or not the alignment according to the modified procedure is sufficiently accurate. Generally, in the case of the QRS complex, the part thereof being of interest and having the higher noise level is a high frequency component thereof.

As mentioned above, analysis of the HF QRS preferably serves as a diagnostic tool for early detection of ischemia. Therefore, various data extraction procedures (unit 84 of FIG. 5) described in the following section focus on the extraction of those parameters currently believed to be diagnostically significant. The skilled person will appreciate that future developments may add new parameters to the list of those believed to be diagnostically significant and may render some or all of those currently so regarded as redundant or otherwise insignificant. The skilled person will thus appreciate the need to modify the data extraction unit 84 in the light of such developments.

In the following, for the sake of simplicity it will be assumed that data extraction procedures described below have access to the following data:

1. An array of aligned noise reduced HF QRS waves.
2. An array of aligned standard ECG waves.
3. For each wave, pointers to its correct location in the raw signal.
4. The raw signal.
5. The band-pass filtered raw signal.
6. Any other parameter calculated at each of the previous stages even if it was not specifically mentioned that it has been stored in any kind of storage device, including, but not limited to, the cross-correlation of each wave with the relevant reference wave, and the S/N ratio in the signal at different stages of the test being carried out on the patient.

The following specific embodiments of the data extraction unit 84 are taken from experiments which explored the 150–250 Hz frequency band. The embodiments are not, of course, in any way limited to those specific frequencies.

As shown by Beker et al, a decrease in the total energy of the HF QRS signal during exercise gives a strong correlation with an ischemic condition of the heart. In what follows the RMS of an HF QRS signal is taken to represent the energy. A decrease in the total energy of the signal during exercise can be looked for in any of the following ways:

1. Choose an arbitrary point during a rest period and compute the RMS of the HF QRS at that point. Compare that value with the RMS value of an HEF QRS at an arbitrary point at peak exercise.
2. Proceed as in 1 above except that the reference point at rest is chosen as the one with minimum RMS value.
3. Proceed as in 1 or 2 above where the reference point during exercise is chosen right after peak exercise.
4. Compute the mean RMS value of the HF QRS over the entirety of a rest stage of the test and compare it to the RMS value at a point of time during an exercise stage.
5. Proceed as in 4 above where a mean RMS calculated for a rest stage is compared with a mean RMS calculated for the exercise stage.
6. Proceed as in 5 where the mean RMS over the exercise stage is taken over a period of relatively stable heart rate.
7. Proceed as in any of 1–6 with any of a set of leads for obtaining ECG signals or any combination of the leads. For example:
   a. The group of leads may include all the precordial leads, all the frontal leads or any other—less standard partition of the leads, for example according to those areas of the heart that they cover.
   b. Proceed as in 1–6 for non-conventional ECG leads corresponding to areas of the heart that are not significant enough in the standard ECG leads.
   c. Proceed as in a or b where the analyzed signal is the vectorial sum of the signals in the group (i.e. given a group of leads, combining it into a single vector by summing all the leads in that group, taking into account their spatial position).
8. Proceed as in any of 1–7 where the RMS is not calculated over the whole QRS complex but over any predetermined portion of the wave. The size and location of the portion of the wave to be examined may be given either in absolute values relative to a fiducial point in the wave (e.g. a portion of 30 ms starting 20 ms after the onset of the signal) or relative to the size of each wave (e.g. that 50% of the wave starting at the beginning of its second quarter).

In a paper by Abboud (Progress in Cardiovascular Diseases Vol XXXV. No. 5 March/April 1993) it has been demonstrated that transient ischemia in patients undergoing percutaneous transluminal coronary angioplasty (PTCA) of a critical stenosis in the left anterior descending (LAD) coronary artery can be detected in the HF QRS wave. It has been shown that the inflation of the balloon (and the transient ischemia it induces) corresponds to a sensible decrease on a graph depicting the normalized cross-correlation coefficient of a (constant) template HF QRS and the real signal. Thus, any of the methods of sections 1–8 of the previous paragraph can be applied using the cross-correlation function in place of the RMS function or in addition thereto.

Thus, analysis of the HF ECG may serve as a very sensitive non-invasive diagnosis tool for the detection of ischemia. Furthermore, the methods for HF ECG analysis suggested herein may be designed to supply on-line results without using hardware additional to standard ECG equipment. Thus, the present embodiments may be readily applied in all situation where standard ECG is used to monitor the heart's condition. Thus, different specific embodiments of the said methods include, among others:

1) Screening exercise tests for early detection of ischemia. The methods suggested herein may serve to gauge the patient's HF ECG signal at rest (i.e. before exercise), the evolution of the signal under stress (i.e between rest and peak exercise) and during a recovery period (i.e. from peak exercise till the heart rate returns to its normal level) carry out a comparison and thus extract diagnostically significant data. The information thus obtained can be compared to the data of previous exercise tests undergone by the same patient, in order to follow the evolution of the cardiac condition over time.

2) Monitoring the evolution over time of coronary perfusion in CAD patients undergoing a drug treatment or during a rehabilitation period after cardiac surgical interventions. That is, using data of several consecutive HF ECG tests over a relatively short period of time (several days or weeks) it is possible to monitor the improvement in the coronary perfusion of the patient in order to assess the effectiveness of the treatment.

3) ER and surgery room on-line monitoring of patients during heart failure such as acute myocardial infarction or during PTCA. On-line analysis of the HF ECG in such situations may help the diagnosis in ERs (whether or not the patient suffers from ischemia) and to assess the immediate improvement of the coronary perfusion during a cardiac surgical intervention.

4) Integration of the embodiments into any (not necessarily cardiac) monitoring systems, including but not in any way limited to standard ECG monitoring.

In addition, the various embodiments of the present invention may be applied to the extraction of a low amplitude signal from input containing a high amplitude signal masking the low amplitude signal. That is, as long as noise is not correlated with the low amplitude signal that it masks the embodiments of the present invention are applicable, even if the noise is not evenly distributed in the spectrum domain. A typical embodiment of the method in such a case is fetal ECG monitoring, where the signal of interest is masked by the mother's much stronger signal. In that case the method is applied to detect the mother's ECG, and to create therefrom a set of dynamically chaining templates that may subsequently be subtracted from the original data, thus to leave only the fetal ECG.

In accordance with the above described embodiments there are thus provided embodiments of the present invention which provide in various aspects:

1) The use of the high frequency part of an ECG signal, more specifically the high frequency components of the QRS complex, in early detection of cardio-vascular infarction, tests involving the high frequency part of the signal being typically more sensitive than the standard ECG signal. In general, a decrease of the HF ECG of the QRS complex during stress test serves as an indication of such a condition.

2) Alignment of high frequency parts of ECG waves using the low frequency parts of the waves.

3) Reducing excessive-noise related artifacts by by selecting waves having highest cross-correlation levels with a reference wave.

4) A noise reduction procedure involving successive averaging of aligned waves, the procedure being modified for minimal distortion of an overall waveform by selecting a predetermined SNR and terminating iteration when the predetermined SNR is reached.

5) Extraction of an RMS of a high frequency component of a QRS complex of an ECG signal to determine whether there is a successive decrease in the level of such an RMS. The presence of such a successive decrease may be used to indicate the probability of the presence of ischemia.

6) Extraction of a cross-correlation function of a high frequency component of a QRS complex of an ECG signal to determine whether there is a successive decrease in the level of such a function. The presence of such a successive decrease may be used to indicate the probability of the presence of ischemia.

Generally, the probability of the presence of any of the conditions referred hereinbefore in the human (or animal) body infers a signal given by a machine to draw the attention of medical personnel to the possibility of the presence of a condition.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

The invention claimed is:

1. A device for reducing noise in signals having successive substantially repetitive portions, comprising:
    an iterative averager operative to superimpose and average said substantially repetitive portions to produce a running average thereof,
    an iteration ender comprising a noise analyzer for determining a noise level in said running average and ending operation of said iterative averager when a noise level reaches a predetermined level,
    an aligner for aligning at least some of said substantially repetitive portions one with another,
    wherein said signal comprises
    first frequency and second frequency components and said aligner comprises a first frequency correlated band pass filter and a second frequency correlated band pass filter to extract respective first and second frequency components, thereby to use said first frequency components to locate an alignment point in successive portions and to use said alignment point to align said second frequency components.

2. A device for reducing noise in signals according to claim 1, wherein said iterative averager is operative to take said successive portions in successive iterative steps.

3. A device for reducing noise in signals according to claim 1, wherein said iteration ender is further operative to end said operation of said iterative averager when said repetitive portions are exhausted.

4. A device for reducing noise in signals according to claim 1, wherein said iteration ender is further operative to end said operation of said iterative averager when said running average reaches a preset maximum of included repetitive portions.

5. A device for reducing noise in signals according to claim 1, further comprising a repetitive portion selector for selecting repetitive portions for passing to said iterative averager, the repetitive portion selector comprising
    a reference portion store for storing a reference portion,
    a cross correlator for computing a cross correlation between a current repetitive portion and said reference portion, and
    a comparator for comparing a result of said cross-correlation with a predetermined threshold to produce a comparison output,
    and wherein said selector is operable to pass said current repetitive portion to said iterative averager in accordance with said comparison output.

6. A device for reducing noise in signals according to claim 5, further comprising a reference portion determination unit associated with said repetitive portion selector, operable to determine as a reference portion any one of a group comprising a first repetitive portion of a current length of said signal, a final result of a running average of a previous set of iterations and a prior determined typical wave.

7. A device for reducing noise in signals according to claim 6, wherein said reference portion determination unit is operable to dynamically change between members of said group over the course of a set of iterations.

8. A device for reducing noise in signals according to claim 6, wherein said reference portion determination unit further comprises a reference portion updater for dynamically updating said reference portion during the course of a set of iterations.

9. A device for noise reduction in a signal according to claim 1, further comprising a signal extractor for extracting said repetitive portion.

10. A device for noise reduction in a signal according to claim 9 comprising an RMS computation unit for calculation of the energy level of segments of wave obtained by averaging a series of said repetitive portions.

11. A device for noise reduction in a signal according to claim 10, further comprising an RMS value analysis unit for detecting a falloff in said RMS energy value over succeeding averages.

12. A device for noise reduction in a signal according to claim 9, comprising a cross-correlation unit for computing the cross correlation coefficient of an average of a series of said repetitive portions and a reference wave.

13. A device for noise reduction in a signal according to claim 12, further comprising a cross-correlation value analysis unit for detecting a falloff in said cross-correlation value over succeeding averages.

14. A device for noise reduction in a signal according to claim 1, wherein said aligner further comprises a cross-correlator for cross-correlating a current input with said running average at a plurality of successive alignments and for aligning said signal on the basis of an alignment giving a maximum cross-correlation.

15. A device for noise reduction in a signal according to claim 14 wherein said aligner further comprises:
    an interpolator for interpolating between said cross-correlations at said successive alignments to determine a higher accuracy sub-sample alignment, and a wave shifter for shifting said current input in accordance with said determined sub-sample alignment.

16. A device for reducing noise in signals having successive substantially repetitive portions, comprising:
- a repetitive portion selector for selecting repetitive portions for passing to an iterative averager, the repetitive portion selector comprising:
- a reference portion store for storing said reference portion,
- a first cross correlator for computing cross correlation between current repetitive portion and said reference portion,
- a comparator for comparing a result of said cross-correlation with a predetermined threshold to produce a comparison output,
- said iterative averager operative to superimpose and average said substantially repetitive portions to produce running average thereof,
- an iteration ender comprising a noise analyzer for determining a noise level in said running average and ending operation of said iterative averager when noise level reaches a predetermined level,
- an aligner for aligning at least some of substantially repetitive portions one with another,
- a reference portion determiner, wherein said reference portion determiner comprising,
- a first store for storing a first set of repetitive portions from said signal,
- a second store for storing a second set of repetitive portions from said signal,
- a second cross correlator for cross-correlating repetitive portions from said second set in turn with repetitive portions from said first set to produce a plurality of cross-correlation results for respective repetitive portions in said second set,
- and a reference selector for selecting one of said repetitive portions in said second set as a reference portion in accordance with its respective cross-correlation results.

17. A device for noise reduction in a signal according to claim 16, wherein said reference selector comprises a threshold level comparator for comparing each cross-correlation result with a threshold and which is operable to select as said reference portion a repetitive portion having a highest number of respective cross-correlation results exceeding said threshold.

18. A device for noise reduction according to claim 16, wherein said reference selector comprises a summation unit for summing cross-correlation results of respective repetitive portions and which reference selector is operable to select as a reference portion a repetitive portion having the highest sum of respective cross-correlation results.

19. A device for noise reduction according to claim 16, wherein said reference selector comprises:
- a threshold level comparator for comparing each cross-correlation result with a threshold, and
- a summation unit for summing cross-correlation results of respective repetitive portions exceeding said threshold,
- and which reference selector is operable to select as a reference portion a repetitive portion having a highest sum of respective cross-correlation results.

* * * * *